US007951544B1

(12) United States Patent
Reed

(10) Patent No.: US 7,951,544 B1
(45) Date of Patent: May 31, 2011

(54) METHOD FOR DETERMINING THE PROGNOSIS OF CANCER PATIENTS BY MEASURING LEVELS OF BAG EXPRESSION

(75) Inventor: John C. Reed, Rancho Sante Fe, CA (US)

(73) Assignee: Sanford-Burnham Medical Research Institute, La Jolla, CA (US)

(*) Notice: Subject to any disclaimer, the term of this patent is extended or adjusted under 35 U.S.C. 154(b) by 961 days.

(21) Appl. No.: 10/030,497

(22) PCT Filed: Jul. 7, 2000

(86) PCT No.: PCT/US00/18758
§ 371 (c)(1),
(2), (4) Date: Jun. 27, 2002

(87) PCT Pub. No.: WO01/04343
PCT Pub. Date: Jan. 18, 2001

Related U.S. Application Data

(63) Continuation of application No. 09/350,518, filed on Jul. 9, 1999.

(51) Int. Cl.
*G01N 33/53* (2006.01)
(52) U.S. Cl. .................................................. 435/7.1
(58) Field of Classification Search ............... 436/64, 436/813; 424/130.1, 9.1; 530/387.1; 435/7.1
See application file for complete search history.

(56) References Cited

U.S. PATENT DOCUMENTS

| | | | |
|---|---|---|---|
| 4,968,603 A | 11/1990 | Slamon et al. ............. | 435/6 |
| 5,188,964 A | 2/1993 | McGuire et al. | |
| 5,447,843 A | 9/1995 | McGuire et al. ............ | 435/6 |
| 5,550,019 A | 8/1996 | Reed ........................ | 435/6 |
| 5,641,866 A | 6/1997 | Reed et al. ................ | 530/387.7 |
| 5,665,539 A | 9/1997 | Sano et al. ................ | 435/6 |
| 5,693,465 A | 12/1997 | Manning et al. ........... | 435/6 |
| 5,862,304 A | 1/1999 | Ravdin et al. ............. | 395/22 |
| 5,882,864 A | 3/1999 | An et al. .................. | 435/6 |
| 6,221,622 B1 | 4/2001 | Love | |

FOREIGN PATENT DOCUMENTS

| | | |
|---|---|---|
| WO | 95/13292 | 5/1995 |
| WO | 97/07387 | 2/1997 |
| WO | 97/48982 | 12/1997 |
| WO | 00/14106 | 3/2000 |

OTHER PUBLICATIONS

Froesch B. A. et al. "BAG-1L Protein Enhances Androgen Receptor Function", 1998, 273 (19), 11660-11666.*
Liao, et al., FEBS Letters, 2001, 503: 151-157.*
Turner et al., Breast Cancer Research and Treatment, 1997, 46(1): 69.*
Froesch et al., Proceedings of the American Association for Cancer Research Annual Meeting, 1998, 89: 13.*
Noordzij et al., J. Urology, 1997, 158: 1880-1885.*
Ballinger et al., "Identification of CHIP, a Novel Tetratricopeptide Repeat-Containing Protein That Interacts with Heat Shock Proteins and Negatively Regulates Chaperone Functions," *Mol. Cell Biology*, 19:4535-4545 (1999).
Elledge et al., "*bcl*-2, p53, and Response to Tamoxifen in Estrogen Receptor-Positive Metastatic Breast Cancer: A Southwest Oncology Group Study," *J. Clin. Oncol.*, 15:1916-1922 (1997).
Fisher et al., "Significance of ipsilateral breast tumor recurrence after lumpectomy," Lancet, 338:327-331 (1991).

Höohfeld and Jentsch, "GrpE-like regulation of the Hsc70 chaperone by the anti-apoptotic protein BAG-1," *EMBO J.*, 16:6209-6216 (1997).
King et al., "Comparison of Immunocytochemical and Steroid-binding Assays for Estrogen Receptor in Human Breast Tumors," *Cancer Res.*, 45:293-304 (1985).
Krajewski et al., "Prognostic significance of apoptosis regulators in breast cancer," *Endocrine Related Cancer*, 6:29-40 (1999).
Markman, M., *Basic Cancer Medicine*, W.B. Saunders Co., Philadelphia, Pennsylvania (1997).
Slamon et al., "Studies of the HER-2/*neu* Proto-oncogene in Human Breast and Ovarian Cancer," *Science*, 244:707-12 (1989).
Takaoka et al., "Anti-cell death activity promotes pulmonary metastasis of melanoma cells," *Oncogene*, 14:2971-2977 (1997).
Takayama et al., "Bag-1 modulates the chaperone activity of Hsp70/Hsc70," *EMBO J.*, 16:4887-4896 (1997).
Takayama et al., "Expression and Location of Hsp70/Hsc-Binding Anti-Apoptotic Protein BAG-1 and Its Variants in Normal Tissues and Tumor Cell Lines," *Cancer Res.*, 58:3116-3131 (1998).
Takayama et al., "An Evolutionarily Conserved Family of Hsp70/Hsc70 Molecular Chaperone Regulators," *J. Biol. Chem.*, 274:781-786 (1999).
Tang et al., "Expression of BAG-1 in Invasive Breast Carcinomas," *J. Clin. Oncol.*, 17:1710-1719 (1999).
Yang et al., "Overexpression of Anti-apoptotic Gene BAG-1 in Human Cervical Cancer," *Exp. Cell Res.*, 247:200-207 (1999).
Yang et al., "Differential Expression of Antiapoptotic Gene BAG-1 in Human Breast Normal and Cancer Cell Lines and Tissues," *Clinical Cancer Research*, 5:1816-1822 (1999). Yang et al., "Enhanced Expression of Anti-Apoptotic Proteins in Human Papillomarvirus-Immortalized and Cigarette Smoke Condensate-Transformed Endocervical cells: Correlation With Resistance to Apoptosis Induced by DNA Damage," *Mol. Carcinoq.*, 22:95-101 (1998).
Yawata et al., "Prolonged cell survival enhances peritoneal dissemination of gastric cancer cells," *Oncogene*, 16:2681-2686 (1998).
Zapata et al., "Expression of multiple apoptosis-regulatory genes in human breast cancer cell lines and primary tumors," *Breast Cancer Research and Treatment*, 47:129-140 (1998).
Borre et al,: "Immunohistochemical BCL-2 and Ki-67 expression predict survival in prostate cancer patients followed expectantly," *Prostate Cancer Prostatic Dis.* 1(5):268-275 (1998).
Kim et al., "c-erbB-2 oncoprotein assay in ovarian carcinoma and its clinical correlation with prognostic factors," *Cancer Letters* 132:91-97 (1998).
Sauter et al., "Nipple aspirate fluid: a promising non-invasive method to identify cellular markers of breast cancer risk," *Br. J. Cancer* 76(4):494-501 (1997).
Turner et al., "BAG-1: A Novel Biomarker Predicting Long-Term Survival in Early-Stage Breast Cancer," *J. Clin. Oncol.* 91(4):992-1000 (2001).
Maher et al., Prognostic Significance of Colony-stimulating Factor Receptor Expression in Ipsilateral Breast Cancer Recurrence, *Clin Cancer Res.* 4:1851-1856 (1998).

* cited by examiner

*Primary Examiner* — Hong Sang
(74) *Attorney, Agent, or Firm* — Jones Day

(57) ABSTRACT

In accordance with the present invention, there are provided methods for determining a prognosis of disease free or overall survival in a patient suffering from cancer. Also provided are methods for predicting the risk of tumor recurrence or spread in an individual having a cancer tumor. Methods for screening a cancer patient to determine the risk of tumor metastasis; methods for determining the proper course of treatment for a patient suffering from cancer; and kits for use in practising the invention methods.

15 Claims, 3 Drawing Sheets

METHOD FOR DETERMINING THE PROGNOSIS OF CANCER PATIENTS BY MEASURING LEVELS OF BAG EXPRESSION

This application is a United States national stage application of PCT/US00/18758, having an international filing date of Jul. 7, 2000, and which claims benefit of priority of U.S. application Ser. No. 09/350,518, filed Jul. 9, 1999.

Portions of the invention described herein were made in the course of research supported in part by NIH grant CA-67329. The Government may have certain rights in this invention.

FIELD OF THE INVENTION

The present invention relates generally to determining the risk of progression or spread of cancers.

BACKGROUND INFORMATION

Prognosis in clinical cancer is an area of great concern and interest. It is important to know the aggressiveness of the malignant cells and the likelihood of tumor recurrence or spread in order to plan the most effective therapy. Breast cancer, for example, is managed by several alternative strategies. One of every nine women currently develops breast cancer at some point in her life. In some cases local-regional therapy is utilized, consisting of mastectomy or lumpectomy with or without radiation, while in other cases when spread of disease is detected or suspected, systemic therapy is instituted, such as chemotherapy or hormonal therapy. Among women with early-stage breast cancers treated with lumpectomy and local radiotherapy, 10-20% will experience local recurrences and 30-40% will develop distant metastatic disease which is often fatal (Fischer et al. 1991, *Lancet* 338:327-331).

Current treatment decisions for individual breast cancer patients are frequently based on (1) the number of axillary lymph nodes involved with disease, (2) estrogen receptor and progesterone receptor status, (3) the size of the primary tumor, and (4) stage of disease at diagnosis. It has also been reported that DNA aneuploidy and proliferative rate (percent S-phase) can help in predicting the course of disease. In addition, the overexpression of the HER2/Neu oncoprotein has been shown to predict breast cancer patients at risk for metastatic disease and novel therapeutic strategies have been developed to target this receptor (Slamon et al. U.S. Pat. No. 4,968,603; Slamon et al. 1989, *Science* 244:707-712). However, even with these additional factors, practitioners are still unable to accurately predict the course of disease for all breast cancer patients. There is clearly a need to identify new markers, in order to separate patients with good prognosis who may not require further therapy from those more likely to recur who might benefit from more intensive treatments.

This is particularly true in the case of breast cancer which has not progressed to the axillary lymph nodes. There is now evidence in prospective randomized clinical trials that adjuvant endocrine therapy and adjuvant chemotherapy beginning immediately after surgical removal of the primary breast tumor can be of benefit in some of these node-negative patients. This has led to official and unofficial recommendations that most if not all node-negative breast cancer patients should be considered for some form of adjuvant therapy. But since the majority (about 70%) of these patients enjoy long-term survival following surgery and/or radiotherapy without further treatment, it may be inappropriate to recommend adjuvant therapy for all of these patients. Accordingly, there is a need for methods to distinguish those node-negative patients who are "cured" from those destined to recur, such that only the latter are treated. Thus, there is a great need for a general method of predicting tumor recurrence or spread in these patients and in cancer patients in general once a primary tumor is detected. The present invention satisfies these needs and provides related advantages as well.

SUMMARY OF THE INVENTION

In accordance with the present invention, there are provided methods for determining a prognosis of disease free or overall survival in a patient suffering from cancer. In one embodiment, it has been found that high levels or "overproduction" of BAG proteins in primary tumor tissue show an unexpected and surprisingly high correlation with lack of tumor recurrence or spread, and therefore long-term disease free or overall survival.

Thus, the present invention advantageously provides a significant advancement in cancer management because early identification of patients at risk for tumor recurrence or spread will permit aggressive early treatment with significantly enhanced potential for survival.

Also provided are methods for predicting the risk of tumor recurrence or spread in an individual having a cancer tumor; methods for screening a cancer patient to determine the risk of tumor metastasis; methods for determining the proper course of treatment for a patient suffering from cancer; and kits for use in practicing the invention methods.

DETAILED DESCRIPTION OF THE INVENTION

Figure 1:
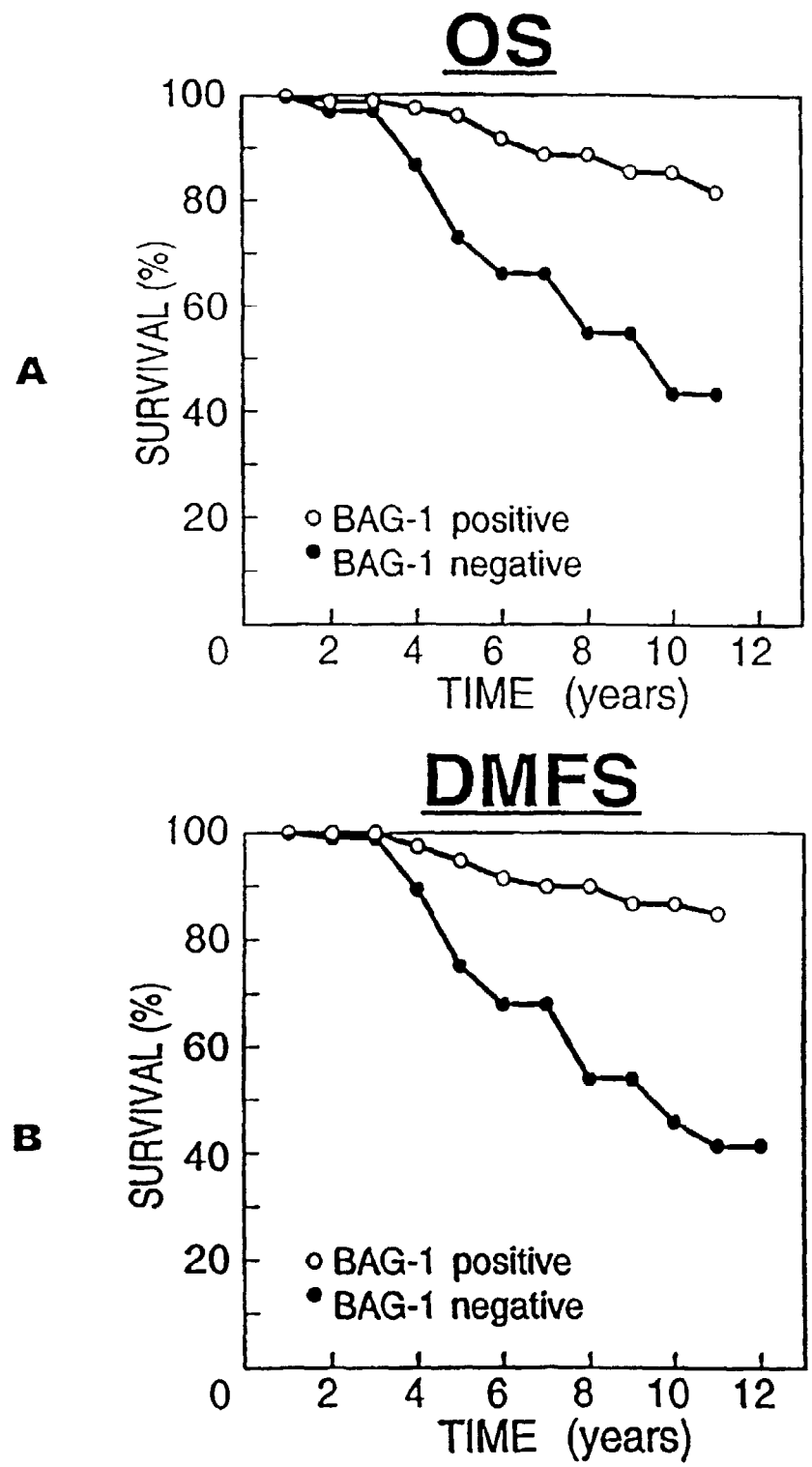
FIG. 1 shows that high BAG-1 Protein levels are associated with longer patient survival in breast cancer patients, as set forth in Example 1. Kaplan-Meier survival curves containing the proportion of early stage breast cancer patients whose tumors contain high (○; referred to in the figure as BAG-1 positive) versus low (●; referred to as BAG-1 negative) levels of BAG-1 protein is plotted against time (years) for overall survival (OS) (top; A) and distant metastasis-free survival (DMFS) (bottom; B).

In accordance with the present invention, methods are provided for determining a prognosis of disease free or overall survival in a patient suffering from cancer, said method comprising:

(a) determining a BAG gene expression level in a cancerous tissue sample from said patient; and (b) classifying said patient as belonging to either a first or second group of patients, wherein said first group of patients having high levels of expression of the BAG gene is classified as having a different likelihood of suffering tumor recurrence or spread than said second group of patients having low levels of expression of the BAG gene.

The invention method takes advantage of a newly discovered correlation between abnormal levels of BAG expression in cancerous cells, and the likelihood of cancer-free survival in patients (see, e.g., the Examples section). The invention method comprises determining the level of expression of BAG in the cancerous tissue of a patient. The patient may then be classified as belonging to a first group of patients having high levels of expression of BAG, or alternatively, to a second group of patients having low levels of expression of BAG. Determination of the prognosis for the patient suffering from cancer may be made by determining whether the group to which the patient has been assigned correlates with a higher or lower likelihood of disease-free or overall survival with respect to the group to which the patient was not assigned.

For example, in one embodiment of the invention, it has been discovered that overproduction or a high level of expression of a BAG gene correlates to patients having a decreased risk of tumor recurrence or spread (e.g., local recurrence or spread and/or metastasis). Thus, in this embodiment, patients belonging to a first group having high levels of expression of a BAG gene are classified as having a decreased risk of tumor recurrence or spread compared to a second group of patients having low levels of expression of a BAG gene. This embodiment is particularly useful in evaluating the prognosis of breast cancer patients.

For example, in this embodiment, when BAG gene expression exceeds a determined basal level (also referred to herein as a reference level), it has been found to become a significant factor in decreased tumor recurrence or spread. When tumor cell determined basal levels are exceeded, a BAG expression level is characterized as "high" or "overproduced" and indicates, particularly in the case of breast cancer, a decreased risk of tumor recurrence or spread. Whereas, the mere presence, without overproduction, of BAG protein expression has not previously been correlated with any risk of tumor recurrence or spread.

In another embodiment of the invention, high levels of expression of a BAG gene correlate to patients having an increased risk of tumor recurrence or spread. Thus, in this embodiment, patients belonging to a first group of patients having high levels of expression of the BAG gene are classified as having an increased risk of tumor recurrence or spread compared to a second group of patients having low levels of expression of the BAG gene.

In yet another embodiment of the invention, low levels of expression of a BAG gene correlate to patients having a decreased risk of tumor recurrence or spread. Thus, in this embodiment, patients belonging to a second group of patients having low levels of expression of the BAG gene are classified as having a decreased risk of tumor recurrence or spread compared to a first group of patients having high levels of expression of the BAG gene.

In another embodiment of the invention, low levels of expression of a BAG gene correlate to patients having an increased risk of tumor recurrence or spread. Thus, in this embodiment, patients belonging to a second group of patients having low levels of expression of the BAG gene are classified as having an increased risk of tumor recurrence or spread compared to a first group of patients having high levels of expression of the BAG gene.

The invention methods are useful in the prognosis of disease-free or overall survival of individuals with neoplastic diseases, including both solid tumors and hematopoietic cancers. Exemplary neoplastic diseases include carcinomas, such as adenocarcinomas and melanomas; and sarcomas, such as various leukemias or lymphomas. Of particular interest are breast cancer, prostate cancer, lung cancer, colon cancer, leukemia, lymphoma, and oral cancer; more particularly breast cancer.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

Depending on the nature of the cancer, an appropriate patient sample is obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques. Alternatively, a body fluid sample, such as a lymph, blood or serum sample, or an exudate fluid sample such as the cancerous organ exudate (e.g., exudate from the breast) may be collected and used as the sample to be analyzed. In the case of leukemias, lymphocytes or leukemic cells will be obtained and appropriately prepared. Similarly, in the case of any metastasized cancer, cells may be drawn from a body fluid such as lymphatic fluid, blood, serum, or a distally infected organ or exudate thereof. While BAG levels will typically be measured within the cancerous cells of a patient, levels of BAG will also be measured in a body fluid sample (e.g., serum) as a result of BAG having been secreted or otherwise released from cells (e.g., by cell rupture).

As set forth herein, the invention method for determining the prognosis of a cancer patient comprises: (a) determining the level of BAG gene expression in cancerous tumor cells of a patient, and (b) classifying the patient as having a either a low or high likelihood of tumor recurrence or spread based on the level of BAG gene expression in the tumor sample or body fluid sample (e.g., serum) of the patient relative to the reference level.

Determining Levels of Bag Gene Expression

Once the patient tissue or cell sample is obtained, prognosis of disease free or overall survival includes determination of the levels of BAG gene expression or amplification in a cancerous tumor. Measurement of BAG gene expression is performed quantitatively such that the level of gene expression can be determined. The BAG expression level is then used to determine the prognosis of disease-free or overall survival of a cancer patient based on the correlations provided herein. This is possible because the likelihood of tumor recurrence or spread correlates with the level of BAG expression in tumor cells. For example, it has been found that when the level of BAG expression is high, the likelihood of metastasis of certain cancers, such as breast cancer, is low. The level of BAG expression may be used as the sole factor in assessing the disease status, or along with the additional factors, including, in the illustrative case of breast cancer, lymph node status, estrogen receptor status, and the like.

As used herein, "BAG gene" refers to the nucleic acid sequence encoding a protein comprising a BAG domain as set forth in Takayama et al. 1999, *Journal of Biological Chemistry* 274:781-786, which is incorporated herein in its entirety.

Exemplary BAG proteins include the various isoforms, preferably human, of BAG-1 (including isoforms such as BAG-1N, BAG-1M, and BAG-1L, see discussion below), BAG-2, BAG-3, BAG-4, BAG-5 proteins, and any other protein which contains a BAG domain and any mutation or partial deletion thereof, including a mutation or partial deletion which results in enhanced or decreased BAG gene expression or in the expression of overactive, underactive, or inactive BAG protein. Other BAG proteins include BAG-1 and BAG-2 proteins from *Caenorhabditis elegans*, and BAG-1A and BAG-1B from *Schizosaccharomyces pombe* (Takayama et al. 1999, supra). Thus, as used herein a BAG protein has a conserved 45-amino acid region near the C-terminus, referred to herein as the BAG domain.

A preferred BAG protein for use herein is human BAG-1. BAG-1 protein was originally identified as a novel regulator of apoptosis by virtue of its ability to bind Bcl-2, a potent blocker of cell death. Since its initial characterization, BAG-1 has been found to interact with not only Bcl-2, but also a number of other proteins which are known to be critical in controlling cell death, including Hsp70/Hsc70, Raf-1, HGF receptor, PDGF receptor, and several steroid hormone receptors.

Figure 3:
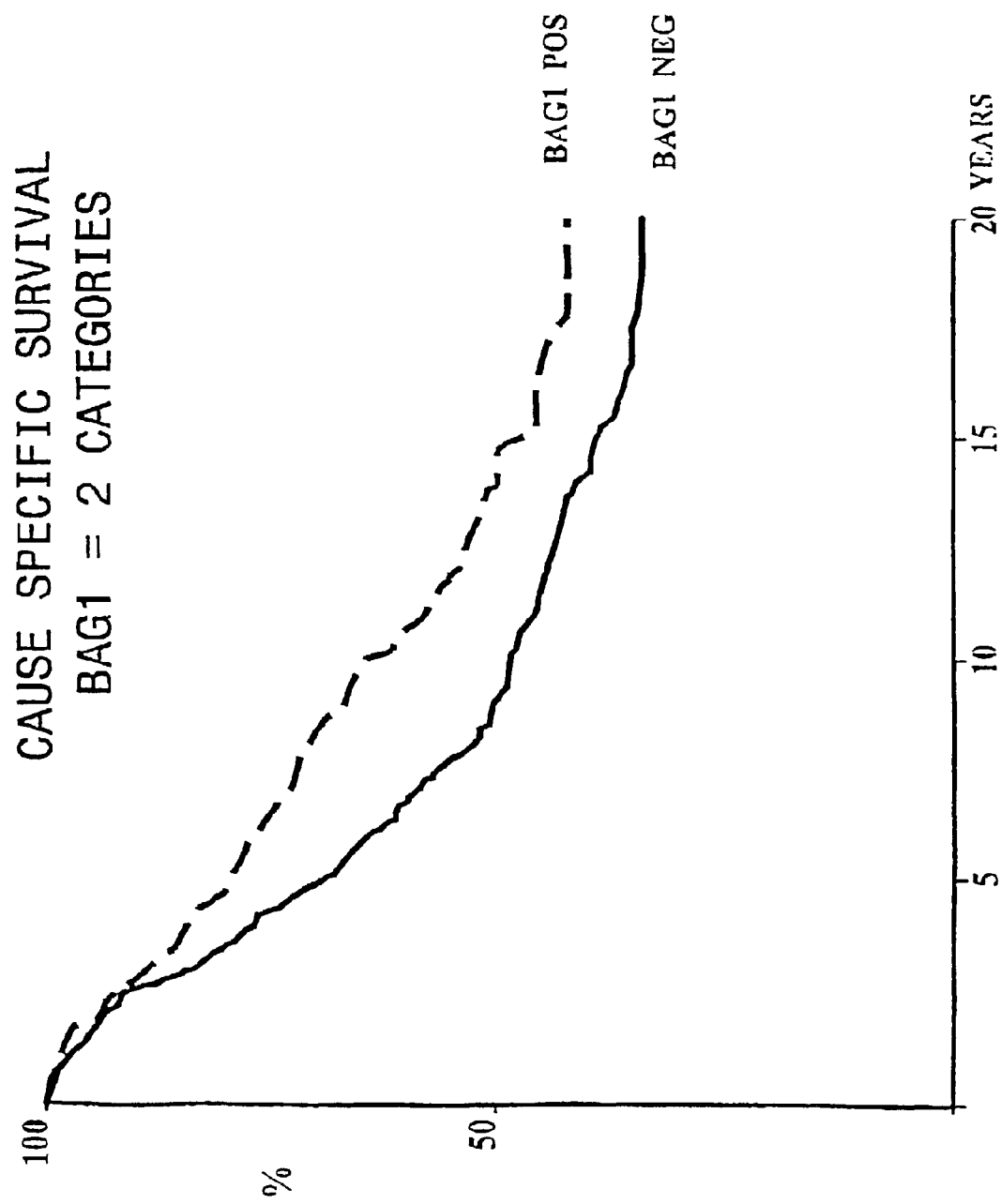
FIG. 3 shows the results of Cause Specific Survival in breast cancer patients with tumor-position lymph-nodes as set forth in Example 2.

Previous studies have shown that in both mouse and humans, there is only a single size of BAG-1 mRNA molecules transcribed, but a plurality of sizes of BAG-1 polypeptides are translated (Takayama et al. 1998, *Cancer Research* 58:3116-3131). In mouse, two isoforms have been identified: the normal length BAG-1 (referred to herein as "BAG-1N"); and a longer BAG-1 polypeptide, or BAG-1L. In human, in addition to the presence of the corresponding BAG-1N and BAG-1L isoforms, a medium length BAG-1 polypeptide, referred to as BAG-1M, is also translated. The cDNA complementary to the BAG-1 mRNA for mouse and human are set forth in U.S. Pat. No. 5,539,094 and in Takayama et al. 1998, supra, (each of which are incorporated herein by reference in their entirety). The polypeptide sequences for the two mouse isoforms BAG-1N and BAG-1L are 219 and 355 amino acids long, respectively (see Takayama et al. 1998, supra). The polypeptide sequences for human BAG-1N (referred to as BAG-1 in FIG. 3C in Takayama et al. 1998, supra), BAG-1M, and BAG-1L are 230, 274 and 345 amino acids in length, respectively.

BAG polypeptides, and particularly BAG-1 (especially BAG-1N and BAG-1L), are present in numerous normal human tissues. Both BAG-1N and BAG-1L have been found to be present at abnormal levels in numerous cancers (Takayama et al., 1998, supra; and Yang et al., 1999, *Experimental Cell Research* 247:200-207), including for example: colon cancer, leukemia, lymphoma, breast cancer, prostate cancer, lung cancer, melanoma, ovarian cancer, cervical cancer, and renal cancer. However, a correlation of BAG expression levels with prognosis of disease-free or overall survival has heretofore been unavailable.

Determination of BAG gene expression or amplification levels may be performed by one or more of the methods known to one of ordinary skill in the art. For example, BAG amplification or expression levels may be determined by detection of (a) a BAG polypeptide, (b) mRNA encoding a BAG protein, (c) a portion of DNA which constitutes a BAG gene, or (d) any combination thereof.

For example, levels of BAG gene expression can be detected by measuring levels of BAG protein using agents that bind specifically to a BAG polypeptide. As used herein, the term "agent that binds BAG protein" refers to any molecule that specifically binds to a BAG protein, including, for example, BAG-1N, BAG-1L, BAG-1M, and/or polypeptide fragments thereof, and thereby detects the level of BAG expression. Such agents are preferably labeled for detection using methods well known to those of skilled in the art. A variety of agents are contemplated for use herein to specifically detect BAG protein, preferably BAG-1, including proteins known to bind specifically to BAG, antibodies to BAG (such as described in U.S. Pat. No. 5,641,866, incorporated herein by reference in its entirety), or peptides which specifically bind BAG. A preferred agent for binding to BAG-1, such as the anti-BAG-1 antibody used herein (See, for example, Takayama et al. 1998, supra, for description of antibody preparation) binds to all isoforms of BAG-1.

Other, non-antibody proteins, may also be used as "agents." For example, BAG proteins are known to specifically bind numerous proteins, such as Bcl-1, Raf-1, HGF-receptor, PDGF-receptor, Hsp70, Hsc70, steroid hormone receptors, and the like. As a result, any of these proteins, or active BAG binding fragments thereof, may be used to specifically bind BAG. An exemplary active binding fragment of a protein which binds BAG-1 (and also BAG-2 and BAG-3) is a BAG binding domain of Hsp70. The ATPase domain of Hsp70 may be expressed in a truncated form, lacking the carboxy-terminal peptide-binding domain. In this form, Hsp70 will not indescriminantly bind proteins in non-native conformations; however, the ATPase domain of Hsp70 is still capable of binding BAG-1 (or BAG-2 or BAG-3) protein. Therefore, an actively binding fragment of a protein known to specifically bind BAG may be used as an "agent" which specifically binds BAG protein.

Antibodies, both monoclonal and polyclonal, may be used as specifically binding agents which bind BAG protein or a polypeptide fragment thereof. Also contemplated herein as BAG binding agents are any mutants of proteins which specifically bind BAG, whether by deletion (as above exemplified), addition (e.g., addition of a GST domain or a GFP domain), or sequence modification (e.g., site-specific mutagenesis), and the like.

It is also contemplated herein that one or more of the BAG specific binding agents may be used in a single assay to measure BAG protein levels. For example, a certain protein known to interact with a specific portion of the BAG-1 protein, such as, for example, a first antibody raised against the N-terminal 60 amino acids of the BAG-1L protein, may be coupled with another specifically binding protein, such as a second antibody raised against a sequence contained in both BAG-1N and BAG-1L. Using these two antibodies in a single assay, the specific levels of the differently translated BAG-1 polypeptides may be measured by differentially measuring the two antibodies.

Preparation of the agent for use in the detection of BAG protein levels will be carried out using the methods of one of ordinary skill in the art, such as the methods exemplified in the Current Protocols in Molecular Biology, and in U.S. Pat. No. 5,882,864. Similarly, detection of BAG protein levels may be carried out using any of the methods known to one of ordinary skill in the art including histochemical staining, Western Blot analysis, immunoprecipitation (or the equivalent thereof for non-antibody agents), and the like. In a preferred embodiment of the invention, the method of detecting BAG protein levels is an immunoassay (such as an ELISA, immuno-PCR, and the like), which includes the use of at least one antibody. Measurement of the polypeptide encoded by a BAG gene may include measurements of fragments of the polypeptide, wherein the fragments arise from transcriptional or translational variants of the gene; or alternatively, differently sized polypeptides arise as a result of post translational modifications including proteolysis of a larger portion of a BAG polypeptide.

An exemplary immuno assay for use in the invention methods for detecting BAG protein levels is an immuno-polymerase chain reaction immuno-PCR assay (described in U.S. Pat. No. 5,665,539, which is incorporated herein in its entirety). Immuno-PCR utilizes an antibody (or other agent which binds BAG) to detect the BAG protein, wherein the antibody (or other agent) is linked to a molecule (typically biotin) which specifically binds a bridging molecule (typically avidin), wherein this bridging molecule is capable of binding a second molecule (typically biotin) attached to a nucleic acid marker. This nucleic acid marker is then amplified using PCR methods. This sensitive detection method is particularly useful when BAG levels are often difficult to detect by other methods, for example, detection of BAG in serum.

Measurement of the polypeptide encoded by a BAG gene may further be carried out to specifically measure: (a) the level of BAG produced in the entire cell, (b) the level of BAG produced in the cytosol, (c) the level of BAG produced in the nucleus, (d) level of BAG present in cell-free extract (e.g., serum), and (e) any combination thereof. Exemplary methods which can be used in such measurements include in situ methods such as histochemical staining, particularly differential staining between the cytosol and the nucleus, and in vitro methods such as Western blot analysis of nuclear extracts, cytosolic extracts, or serum.

Detection of levels of mRNA encoding BAG may also serve as an indicator of BAG expression. The methods used to detect mRNA levels will include the detection of hybridization or amplification with the mRNA encoding BAG. This detection may be carried out by analysis of mRNA either in vitro or in situ (e.g., in a tissue sample) using one of the methods known to one of ordinary skill in the art as exemplified in the Current Protocols in Molecular Biology (John Wiley & Sons, 1999); in U.S. Pat. No. 5,882,864; and the like. A BAG mRNA detected will be any RNA transcript of a BAG gene, or fragment thereof.

Detection of the DNA encoding BAG may also be used as an indicator of BAG expression. A plurality of changes from wild type in the portion of DNA which constitutes a BAG gene may influence levels of gene expression. For example, gene amplification will provide more copies of a BAG gene within each cell, thereby facilitating the manufacture of an increased number of mRNA molecules encoding BAG, which may result in an increased level of BAG protein within the cell. In another example, gene translocation or partial gene deletion may have an effect on the rate of gene expression by, for example, decreasing the ability of a repressor protein to repress BAG transcription, resulting in higher levels of BAG protein within the cell. Detection of the portion of DNA which constitutes a BAG gene may have application by indicating the occurrence of gene amplification, translocation, mutation, partial deletion, or other modification of the copy number, sequence, location, or accessibility of a BAG gene which results in abnormal levels of expression of a BAG gene.

Detection of the DNA constituting a BAG gene may take place by a variety of methods known to those of skill in the art. Such methods will typically include the detection of hybridization to the DNA constituting a BAG gene, or amplification of the DNA constituting a BAG gene. This method may be carried out by analysis of cellular DNA either in vitro or in situ. Numerous methods for carrying out this detection are known to those of ordinary skill in the art, as exemplified in the Current Protocols in Molecular Biology, and in U.S. Pat. No. 5,882,864, which is incorporated herein in its entirety.

Classifying the Patient

The classification of particular patients requires comparing the level of BAG gene expression in the tumor cells of a patient to a reference level (also referred to as a basal level). For example, after measuring the BAG expression level of the cells in a cancerous tumor of a patient, the measured level is compared to a reference level. This reference level is a level of expression of BAG used to evaluate the level of expression of BAG in cancerous cells of a patient. Specifically, when the level of BAG expression in the cancerous cells of a patient are higher than the reference level, the cells will be considered to have a high level of expression, or overproduction, of BAG. Conversely, when the level of BAG expression in the cancerous cells of a patient are lower than the reference level, the cells will be considered to have a low level of expression, or underproduction, of BAG.

As used herein, the terms "high level" or "overproduction" of BAG gene expression is related to a level of BAG gene expression above a determined basal level and is likely different for each cancer type. Thus, in accordance with the present invention a reference or basal level of BAG gene expression in a particular cancer cell type is identified as a "cutoff" value, above which there is a significant correlation between the presence of BAG gene expression and increased or decreased tumor recurrence or spread. Those of skill in the art will recognize that some "cutoff" values are not sharp in that clinical correlations are still significant over a range of values on either side of the cutoff; however, it is possible to select an optimal cutoff value (e.g. varying H-scores, and the like) of BAG gene expression for each cancer cell type. It is understood that improvements in optimal cutoff values could be determined, depending on the sophistication of statistical methods used and on the number and source of samples used to determine reference or basal values for the different cancer cell types.

Such "overproduction" is not typically calculated in terms of absolute BAG gene expression or protein levels, but is determined using relative measurements. These relative measurements are illustrated for quantitation purposes with an "internal standard;" however, it will be appreciated that other standards or methods of determination may be used, such as comparison with external standards, BAG mRNA measurements, measurement of the DNA constituting a BAG gene, absolute values of the protein or mRNA or DNA levels, and the like.

The reference level may be determined by a plurality of methods, provided that the resulting reference level accurately provides a level of BAG expression above which exists a first group of patients having a different risk of tumor recurrence or spread than that of a second group of patients having BAG expression levels below the reference level. The reference level may be determined by, for example, measuring level of expression of BAG in non-tumorous cancer cells from the same tissue as the tissue of the cancer cells to be tested. The reference level may also be a level of BAG expression of in vitro cultured cells which may or may not have been manipulated to simulate tumor cells, or may have been manipulated in any other manner which yields expression levels which accurately determine the reference level.

It is important to recognize that reference levels are not necessarily the levels, of BAG expression found in cultured cell lines used to provide internal standards. Rather, these may be reference level amounts of BAG gene expression (e.g., BAG protein, BAG mRNA, and the like) that occur in tumor cells. It is, for example, possible that a high level of BAG gene expression in a tumor sample will have a relatively lower expression level than the corresponding BAG protein expression level in an internal standard.

The reference level may also be determined by comparison of BAG expression levels in populations of patients having the same cancer. This may be accomplished by histogram analysis, in which the entire cohort of patients tested are graphically presented, wherein a first axis represents the level of BAG expression, and a second axis represents the number of patients in the cohort whose tumor cells express BAG at a given level. Two or more separate groups of patients may be determined by identification of subsets populations of the cohort which have the same or similar expression levels of BAG. Determination of the reference level may then be made based on an expression level which best distinguishes these separate groups.

Verification that the reference level distinguishes the likelihood of tumor recurrence or spread in cancer patients expressing below-reference levels of BAG versus cancer patients expressing above-reference levels of BAG is carried out using single variable or multi-variable analysis. These methods determine the likelihood of a correlation between one or more variables and a given outcome. In the specific case, the methods will determine the likelihood of a correlation between BAG expression levels (or BAG expression levels coupled with another variable) and disease-free or overall survival of cancer patients. Any one of a plurality of methods well known to those of ordinary skill in the art for carrying out these analyses may be used. Examples of single variable analysis is the Kaplan-Meir method or the log-rank test. An example of multi-variable analysis is the Cox proportional-hazards regression model.

Population-based determination of reference levels (e.g., histogram analysis) is carried out using a cohort of patients sufficient in size in order to determine two or more separate groups of patients having different BAG expression levels. Typically, such a cohort comprises at least 25 patients, preferably 50 patients, more preferably 75 patients, and yet more preferably at least 100 patients. Similarly, verification of determined reference levels will also comprise at least 25 patients, preferably 50 patients, more preferably 75 patients, and yet more preferably at least 100 patients.

The reference level may be a single number, equally applicable to every patient, or the reference level may vary, according to specific subpopulations of patients. For example, men might have a different reference level than women for the same cancer. Furthermore, the reference level might be some level determined for each patient individually. For example, the reference level might be a certain ratio of BAG expression in the tumor cells of a patient relative to BAG expression in non-tumor cells within the same patient. Thus the reference level for each patient may be proscribed by a reference ratio of BAG expression, wherein the reference ratio may be determined by any of the methods for determining the reference levels described above.

Further, while the reference level described above discusses a number which separates two groups of patients, it is within the scope of the invention that numerous reference values might exist which separate a plurality of populations. For example, two reference values may separate a first group of patients with high levels of BAG expression from a second group of patients with intermediate levels of BAG expression, and from a third group of patients with low levels of BAG expression. The number of different reference levels may be sufficient to proscribe a curve, such as a continuous line, which describes the likelihood of disease-free or overall survival in a patient as a function of BAG expression level in that patient. Such a curve will constitute a "continuous" BAG reference level, where the likelihood of disease free or overall survival in a patient is portionional to the level of BAG expression level in that patient.

The reference level can also represent the level of BAG protein in one or more compartments of the cell. Typically, the reference level will represent the level of BAG protein in (a) the whole cell, (b) the nucleus, or (c) the cytosol. This level will be useful when cell compartmentalization of BAG protein correlates with the risk of tumor recurrence or spread of a certain cancer. For example, it has been observed that the level of BAG protein is higher in the cytosol of patients with low risk of breast cancer recurrence or spread than the cytosolic BAG protein level of patients with high risk of breast cancer recurrence or spread, despite the fact that the level of BAG expression in the nucleus can be roughly equivalent. Similarly, the reference level may be a ratio of levels of BAG protein in the different compartments (e.g., the ratio of nuclear BAG protein to whole cell BAG protein, or the ratio of nuclear BAG protein to cytosolic BAG protein).

It is also contemplated herein that the reference level can represent the level of expression of a single form of BAG (e.g., BAG-1N, BAG-1M, BAG-1L, BAG-2, BAG-3, BAG-4, OR BAG-5). This reference level will be useful when a single translated form of BAG correlates with the risk of tumor recurrence or spread, of a certain cancer. For example, it may be observed that the level of BAG-1L expression is higher in patients with low risk of lung cancer recurrence or spread than the level of BAG-1L expression in patients with high risk of lung cancer recurrence or spread, despite the fact that the level of total BAG-1 expression (i.e., the sum of BAG-1N, BAG-1M, or BAG-1L expression levels) is the same for all patients. Similarly, the reference level may be a ratio of levels of expression for different forms of BAG (e.g., the ratio of BAG-1N to BAG-1L, the ratio of BAG-2 to BAG-3, and the like).

The reference level of BAG expression may further be used in conjunction with another variable found to be a statistically significant indicator of the likelihood of disease-free or overall survival for a specific cancer. Such indicators include the presence or levels of biomarkers of such as other proteins (e.g., ras, Bcl-2, and the like), or may be clinical or pathological indicators (e.g., age, tumor size, tumor histology, clinical stage, and the like). For example, clinical stage of the cancer is also be a statistically significant indicator of disease-free or overall survival (in addition to BAG expression level), wherein the reference level of BAG expression may vary according to the clinical stage of the cancer. For example, levels of BAG expression, preferably high levels of BAG-1, in conjunction with clinical stage I of a cancer for a given patient, are particularly preferred indicators for increased likelihood of disease free or overall survival.

Hence, the reference level of BAG expression may vary as a function of another statistically significant indicator of disease-free or overall survival for a specific cancer.

Those of skill in the art will recognize that it is also possible to measure levels of BAG proteins in body fluid, such as serum. Tumors are known to readily shed cells which, after release into the bloodstream, may burst due to cell fragility. For example, it is contemplated herein that overexpression of BAG-1 observed in approximately ⅔ of breast cancer patients results in increased secretion and/or release of BAG-1 protein into serum. Thus, detection of any BAG levels, preferably high BAG-1 levels, present in body fluid (e.g., serum) is contemplated for use in the invention methods to determine a prognosis of disease free or overall survival in a manner analogous to that demonstrated with the tissue samples. Very small quantities of BAG can be measured in body fluid, for example, using anti-BAG antibodies in immuno-PCR methods as described herein.

Accordingly, it is contemplated herein that the reference levels may represent the level of BAG present in a body fluid sample, such as serum. Invention methods that measure the level of circulating BAG (i.e., the level of BAG in blood or serum), preferably BAG-1, will have a particularly preferred application to early diagnosis and screening, and early determination of risk of cancer recurrence or spread, for patients with abnormal levels of BAG (e.g., high levels) in their serum.

After the levels of expression of BAG in the tumor cells of a patient have been determined and compared to a reference level, the patient is then classified into a group having a certain likelihood of disease free or overall survival. Then the likelihood of disease-free or overall survival for the patient is assessed based on the likelihood of disease-free or overall survival for patients in that group. For example, the tumor cells of a specific breast cancer patient may be determined to have high levels of BAG expression relative to a reference level. This patient would then be classified into a group of patients having high levels of BAG expression. Since, in accordance with the present invention, it has been discovered that there is an increased likelihood of disease-free or overall survival for the group of patients expressing high levels of BAG-1 in breast cancer cells (relative to those expressing low levels of BAG-1 in breast cancer cells), the specific breast cancer patient would be considered to have an increased likelihood of disease free or overall survival.

In another embodiment of the present invention, a method is provided for prognosis of disease-free or overall survival of individuals having a cancer tumor. In particular, the method comprises determining whether BAG protein is overproduced in a sample of such a tumor, wherein such an overproduction correlates positively with disease-free or overall survival. Thus, patients who produce high levels of BAG protein have an increased likelihood of survival relative to patients producing low levels of BAG protein.

Another embodiment of the invention provides a method for screening a cancer patient to determine the risk of tumor metastasis. The method comprises determining the level of amplification or expression of a BAG gene in a cancerous tissue sample from the patient. A patient found to have high levels of amplification or expression of the BAG gene, relative to a reference level, is classified as being less likely to suffer tumor metastasis or having a increased chance of survival.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Therefore, the present invention contemplates a method of determining the risk of further growth of one or more cancerous tumors in an organ or body part which is not directly connected to the organ of the original cancerous tumor.

In yet another embodiment of the invention, methods are provided for the determination of levels of BAG expression in cancer patients at an early stage of tumor development. As used herein, the term "stage", when applied to tumor development, refers to the degree of progression of a tumor. Various stages of tumor development are well known to those of skill in the art, as exemplified in Markman 1997, *Basic Cancer Medicine*. Stages of different cancers are defined according to different criteria, typically using the Tumor-Node-Metastasis (TNM) system. For example, stage I of breast cancer requires no lymph node involvement, and stage II of breast cancer involves either no lymph node involvement and a large primary tumor, or initial lymph node involvement and a small primary tumor (see Markman, supra, pages 35 and 36). Similar descriptions of the various clinical stages can be found in Markman, supra, for lung cancer (pages 54 to 55), and prostate cancer (pages 64 to 65), colon cancer (pages 78 to 79) and ovarian cancer (page 38 to 39). Early stages of tumor development shall be understood to refer to stages in tumor development in which the tumor has detectably spread no further than the lymph nodes local to the organ of the primary tumor. Typically, early stages will be considered to be stages I and II. As used herein, the phrase, "prior to lymph node involvement" refers to the detectable presence of cancer cells in the organ of the primary tumor, but the lack of a detectable presence of cancer cells in any lymph nodes, including the lymph nodes closest to the organ of the primary tumor.

The predictive value of the method of the invention will be particularly effective in the case of patients in the early stages of cancer. This is because the method of the invention is advantageously effective in determining the risk of metastasis in patients who demonstrate no measurable metastasis at the time of examination. One of ordinary skill in the art would appreciate that the prognostic indicators of survival for cancer patients suffering from stage I cancer may be different from those for cancer patients suffering from stage IV cancer. For example, prognosis for stage I cancer patients may be oriented toward the likelihood of continued growth and/or metastasis of the cancer, whereas prognosis for stage IV cancer patients may be oriented toward the likely effectiveness of therapeutic methods for treating the cancer.

In another embodiment of the invention, a kit is provided to determine the levels of BAG expression in the cancerous tumor cells of the patient. Such a kit will comprise a reagent for detecting either the DNA encoding BAG, the mRNA encoding BAG, the BAG polypeptide, or any combination thereof. The reagent will comprise one or more molecules capable of specifically binding a nucleic acid sequence (DNA or RNA) encoding BAG, or the BAG polypeptide.

The kit may comprise one or more nucleic acid reagents for the detection of either DNA encoding BAG, mRNA encoding BAG, or both. The one or more nucleic acid reagents may be used for hybridization or amplification with the DNA and/or mRNA encoding BAG. The kit may comprise one or more pairs of primers for amplifying the DNA and/or mRNA encoding BAG. The kit may further comprise samples of total mRNA derived from tissue of various physiological states, such as normal, and metastatically progressive tumor, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting the DNA and/or mRNA encoding BAG in cancer cells in a biological sample comprising oligonucleotide probes effective to bind with high affinity to DNA and/or mRNA encoding BAG in vitro or in situ and containers for each of these probes.

In a further embodiment, the invention encompasses a kit for use in determining the level of BAG expression in a biological sample comprising one or more agents, such as, for example, one or more antibodies, specific for one or more BAG polypeptides. In one particular embodiment, the kit will comprise one or more agents and one or more nucleic acid markers wherein the agents and nucleic acid markers are modified in a fashion appropriate for carrying out immuno-polymerase chain reaction assays.

Another embodiment of the invention provides a method for determining the proper course of treatment for a patient suffering from cancer. This method comprises determining the level of expression of a BAG gene in cancerous tissues from a patient. Then, a first group of patients is identified as having low levels of expression of a BAG gene in the cells. This first group of patients may require treatment proper for patients having a lesser chance of survival or decreased time to tumor recurrence or spread. The method further comprises identifying a second group of patients as having high levels of expression of a BAG gene in the cells. This second group of patients may require treatment proper for patients having a greater chance of survival and being less likely to suffer tumor recurrence or spread.

Appropriate treatments for patients having greater or lesser chances of survival will be determined, with proper consideration of other factors, by one of ordinary skill in the art according to the available therapeutic methods. As used herein, "course of treatment" shall be understood to represent the treatment (e.g., surgery, chemotherapy, radiation, and the like) of a patient after diagnosis for cancer, and the span of time during which the patient is treated. Hence, a point in time considered to be "during the course of treatment" shall represent any time between the initiation of the course of treatment and the termination of the course of treatment.

In a further embodiment of the invention, a method is provided for monitoring the effectiveness of a course of treatment for a patient suffering from cancer. This method comprises:
 (a) determining a first BAG gene expression level in a cancerous tissue sample or a body fluid sample from said patient prior to said treatment; and
 (b) subsequently determining a second BAG gene expression level in a cancerous tissue sample or a body fluid sample from said patient during said treatment.
Comparison of said first BAG expression level with said second BAG expression level will then indicate the effectiveness of said treatment.

As used in the context of a course of treatment, "effectiveness" refers to the ability of the course of treatment to decrease the risk of tumor recurrence or spread and therefore to increase the likelihood of disease-free or overall survival of the patient. This method will have particular utility when the level of BAG expression in the tumor cells of a patient is abnormal compared to the level of BAG expression in the non-tumor cells of the patient. Comparison of the first and second BAG expression levels will thereby serve to indicate whether BAG expression level is returning to that of non-tumor cells, implying a more effective course of treatment, or whether BAG expression level is remaining abnormal or increasing in abnormality, implying a less effective course of treatment. Levels of BAG expression may be determined using a plurality of samples from the patient, as described herein. A preferable sample form for this embodiment shall be a body fluid sample, such as serum sample, an exudate sample, and the like.

This embodiment of the invention is particularly useful when combined with the method of determining the risk of tumor recurrence or spread in a cancer patient, and thereby determining the proper course of treatment in a cancer patient. Specifically, the proper course of treatment of a cancer patient may be determined by determining the level of BAG expression in a sample from a patient, then classifying the patient's likelihood of disease-free or overall survival according to the level of BAG expression. The course of treatment may then be monitored, according to the present embodiment of the invention, on one or more occasions to determine the effectiveness of the course of treatment.

In a further embodiment of this invention, a method is provided for determining a prognosis of disease free or overall survival in a patient suffering from cancer. This method comprises:
 (a) determining a BAG activity level in a cancerous tissue sample or body fluid sample from said patient; and
 (b) classifying said patient as belonging to either a first or second group of patients, wherein said first group of patients having high levels of BAG activity is classified as having a different likelihood of suffering tumor recurrence or spread than said second group of patients having low levels of BAG activity.

As used herein, "BAG activity level" or level of "BAG activity" refers to the level of active, uninhibited BAG polypeptides present in tumor cells or body fluid, and the degree of activity of these polypeptides. Hence, level of activity shall be influenced by a plurality of factors including: levels of BAG, presence of less active or more active forms (including isoforms) of BAG, presence of less active or more active mutants of BAG, presence of proteins or other molecules which increase BAG activity, presence of proteins or other molecules which decrease BAG activity. For example, levels of an antagonist to BAG, such as Hip (an antagonist to BAG-1, see for example Hohfeld and Jentsch 1997, *EMBO J* 16:6029-6216), will be understood to commensurately lower BAG activity even if BAG protein levels remain unchanged. Determination of BAG activity shall therefore be carried out by a plurality of methods, including: assay of biological activity of BAG (such as ability to prevent cell death or other apoptotic assays, see, for example, U.S. Pat. No. 5,550,019), assay of BAG protein levels, assay of the mRNA encoding a BAG protein, assay of the DNA which constitutes a BAG gene, assay of proteins (or the mRNA or DNA encoding the proteins) or other molecules which increase or decrease BAG activity, and any combination thereof.

All U.S. patents and all publications mentioned herein are incorporated in their entirety by reference thereto. The invention will now be described in greater detail by reference to the following non-limiting example.

EXAMPLES

1.0 BAG1 Immunostaining Predicts Longer Survival in Breast Cancer Patients with Tumor-Negative Lymph-Nodes The role of BAG1 (also known as RAP46 and HAP-1) immunostaining for prognostic evaluation of women with breast cancer was assessed for patients with negative lymph-node biopsies (i.e. no evidence of tumor in axillary nodes which have been surgically removed for histological examination) by analysis of a cohort of women with stage-I disease. This example illustrates the determination of the reference level of BAG-1 expression in breast cancer patients, and evaluation of the accuracy of the reference level in predicting disease-free or overall survival of separate groups having different BAG-1 expression levels.

A retrospective correlative analysis was performed of BAG-1 using a monoclonal antibody capable of detecting BAG-1N, BAG-1M and BAG-1L (see Takayama et al., 1998, supra). Estrogen Receptor (ER), Progesterone Receptor (PR), HER2/Neu, p53, Bcl-2, Bax, which have all been implicated in breast cancer formation, were also assayed. Immunohistochemical methods were carried out on archival paraffin blocks derived from 116 women with early-stage (stage I: n=73, 63%; and stage-II: n=43, 37%) breast cancer who were treated with lumpectomy followed by radiation therapy to the intact breast using a median dose of 48 Grays (Gy) followed by an electron boost to the lumpectomy site to yield a total median dose of 64 Gy. There were 17/116 (15%) patients treated with adjuvant systemic chemotherapy and 20/116 (17%) patients treated with tamoxifen therapy. The patients had a median follow-up of 12.4 years, with a minimum follow-up of 4 years (Table 1).

TABLE 1

Characteristics of breast cancer cases

| DATA | No. | % |
|---|---|---|
| Number of patients | 116 | NA |
| Mean age (yrs.) | 55 | NA |
| Infiltrating ductal cancer | 103 | (89%) |
| Infiltrating lobular cancer | 9 | (8%) |
| Infiltrating medullary cancer | 4 | (3%) |
| Median follow-up (yrs.) | 12.4 | NA |
| Stage I/II | 116 | (100%) |
| Stage I | 73 | (63%) |
| Stage II | 43 | (37%) |
| Mean pathologic size (cm) | 1.8 | NA |
| Axillary dissection | 62 | (53%) |
| Positive lymph nodes | 13 | (11%) |
| Estrogen receptor positive | 49 | (42%) |
| Adjuvant chemotherapy | 17 | (15%) |
| Adjuvant tamoxifen | 20 | (17%) |
| Metastatic Disease | 35 | (30%) |

The characteristics of patients used for this study are summarized: number (left column); percentage (right column). Metastatic disease indicates the number (and percentage) of patients who developed clinically detectable metastatic disease after diagnosis and treatment.

Immunostaining was carried out by colorimetric antibody detection using diaminobenzidine (brown) followed by hematoxylin (blue) counterstaining of nuclei. Immunostaining of the invasive component of breast cancers was scored according to intensity (0-4, wherein 0 is no staining and 4 is the most intense staining) and percentage of immunopositive cells (0-100%, for a minimum of 200 cells), evaluating the entire tissue-section, with the pathologist blinded to clinical details. Histo-staining (H)-scores (0-400) were obtained by determining the product of intensity (0-4 scale) and percentage (0-1000). To set cut-offs for dichotomization of data into groups having high and low levels of expression, the H-score data for the entire data-set were displayed as dot-histograms with H-score on the x-axis and the number of patient samples having a given H-score on the y-axis. An H-score $\geq 150$ was determined by this approach to be appropriate for use as a cut-off for high levels of BAG-1 expression. H-score data were displayed as histograms and dichotomized into high versus low expression level groups using optimized cut-offs for BAG-1 (H-score>150), Bcl-2 (H-score$\geq$180), and Bax (H-score$\geq$140). Immunoscoring for ER, PR, p53, and HER2/Neu was performed by established criteria (King et al., 1985, *Cancer Research* 45: 293-296).

BAG-1 is known to be present in the nuclei of some types of cells and nuclear immunostaining is normal for breast epithelium, whereas strong cytosolic immunostaining is abnormal here (Takayama et al. 1998, supra). This phenomenon was confirmed in the present example: compared to normal breast epithelium (NBE) cells, which were often present along with tumor cells in the same tissue-sections, cytosolic immunostaining for BAG-1 was clearly upregulated within the invasive breast cancer cells, with elevated levels of protein observed for 77/116 (66%) or roughly two-thirds of early-stage breast cancers compared with 9/83 (11%) of NBE (p<0.001).

Some of the same tumor specimens also contained histologically evident ductal carcinomas in situ (DCIS); high levels of BAG-1 nuclear immunostaining were found in 9/12 (75%) and 6/12 (50%) sections had high levels of cytoplasmic BAG-1 protein levels in DCIS specimens, suggesting that upregulation of BAG-1 can occur as a relatively early event in tumorigenesis and the translocation of protein from the nucleus to the cytoplasm may be important in cellular transformation.

Immunostaining data were correlated with distant metastasis-free survival (DMFS) and overall survival (OS). Kaplan-Meier analysis revealed that elevated levels of BAG-1 were significantly associated (i.e., p$\leq$0.05) with longer DMFS (p<0.001) and OS (p<0.001) (FIG. 1). The group of patients having high BAG-1 protein levels (BAG-1 positive) experienced better 10-year DMFS than the group of patients having low (BAG-1 negative) BAG-1 protein levels (90% high group vs. 40% low group) and OS (84% high group vs. 40% low group). Among the other biomarkers evaluated, only Bcl-2 was significant in univariate analysis as a predictor of longer DMFS (p<0.001) and OS (p<0.001). ER, PR, HER2/Neu, p53, and Bax were all insignificant in predicting survival for this cohort of patients. Among clinical and pathological variables (e.g., age; tumor size; stage; tumor histology), only clinical stage I versus clinical stage II was significant in univariate analysis for predicting survival.

In multivariate models using Cox-regression analysis with variables including BAG-1, Bcl-2, Bax, p53, ER, PR, HER2/Neu, age and clinical stage, only BAG-1 retained statistical significance as a predictor of DMFS (p=0.008) and OS (p=0.02). All other biomarkers failed to reach clear statistical significance and clinical stage (stage I versus stage II) was significant only for DMFS (p=0.029) but not OS. Thus, patients whose tumors contain high levels of cytosolic BAG-1 protein are more likely to enjoy long-term survival and freedom from tumor recurrence or spread and distant metastases, compared to those with tumors containing low levels of cytosolic BAG-1. These results demonstrate that BAG represents a novel and independent prognostic factor which is associated with favorable outcome in patients with early-stage breast cancer.

2.0 BAG1 Immunostaining Predicts Longer Survival in Breast Cancer Patients with Tumor-Positive Lymph-Nodes To address the role of BAG1 immunostaining as a prognostic factor for women with node-positive disease, an immunohistochemical evaluation using the anti-BAG1 monoclonal antibody described in Example 1.0 was performed of tumor specimens derived from a cohort of 342 patients with node-positive breast cancer, 179 of whom were treated with surgery alone and 209 of whom underwent surgical resection followed by 12 monthly cycles of cyclophosphamide, methotrexate, fluorouracil ("CMF") adjuvant therapy. The percentage of tumor cells with cytosolic BAG1 immunopositivity was estimated by light-microscopic evaluation, and the data were gathered into quartiles, representing 0-10%, 11-50%, 51-80%, and >80% immunopositive tumor cells.

Figure 2:
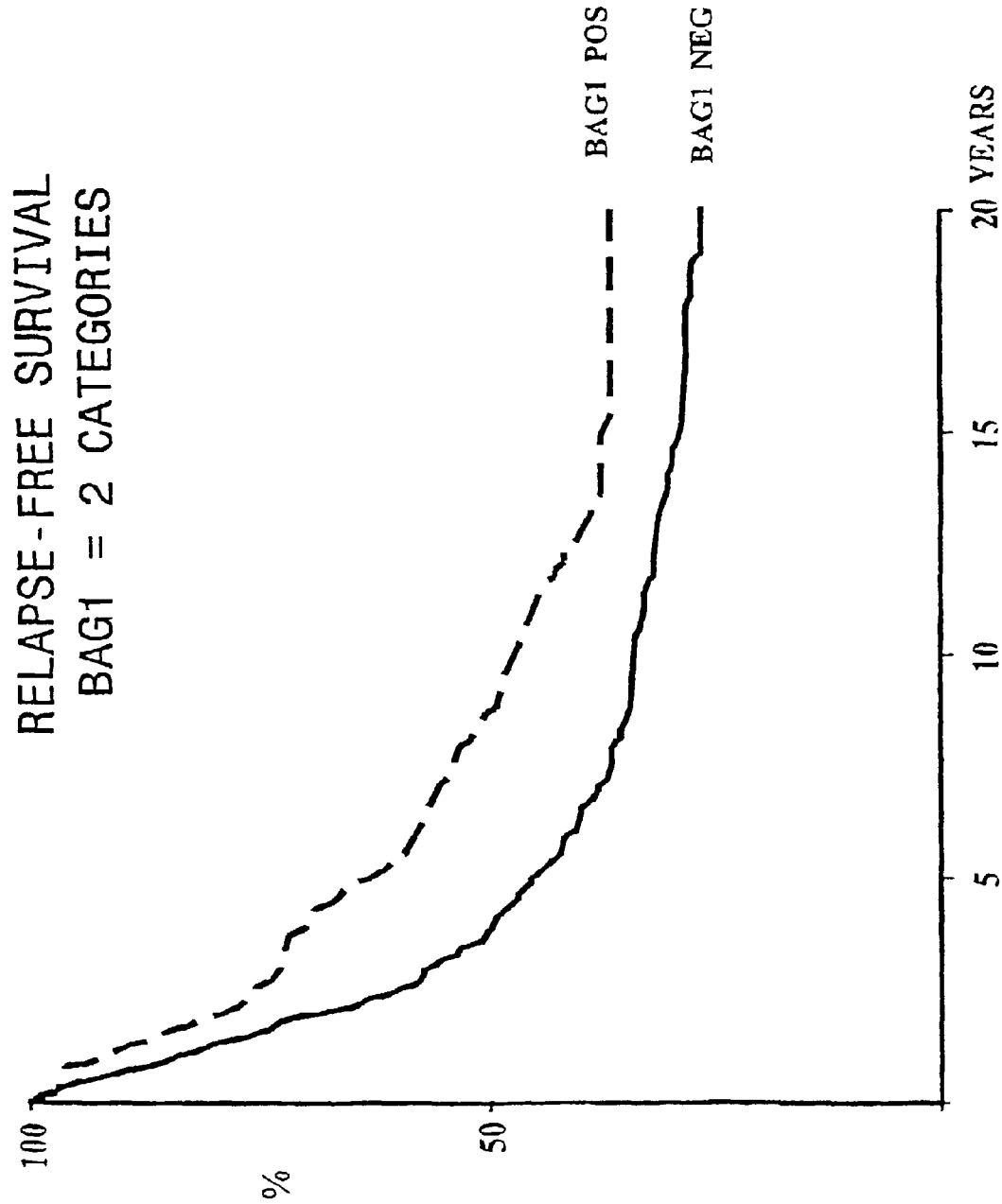
FIG. 2 shows the results of Relapse-Free Survival in breast cancer patients with tumor-position lymph-nodes as set forth in Example 2.

Correlations of the data with relapse-free survival (RFS) and cause-specific survival (CSS) by the Kaplan-Meyer method revealed that the first 3 quartiles behaved similarily, while the fourth quartile (>80% BAG1 immunopositive tumor cells) was significantly different. Examining the entire cohort of 342 patients, higher levels of BAG1 immunostaining (>80% positive) were associated with longer RFS and CSS, as determined by univariate analysis (p=0.05 for both RFS and CSS) (see FIGS. 2 and 3). For example, the percentage of patients not dead due to cancer was 42% among patients whose tumors contained >80% BAG1 immunopositive malignant cells compared to 34% for patients whose tumors contained lower percentages of BAG1 positive cells (Table 2). Whether the patients did or did not receive adjuvant CMF therapy, whether their tumors expressed or did not express Estrogen Receptors (ER), and the number of positive nodes (>3 vs <3) were also of prognostic significance. Other variables were not predictive of outcome, including menopausal status, tumor size (<2 cm versus >2 cm), or other biomarkers such as Bcl-2 (Table 2) and p53.

TABLE 2

Results at 20 yrs
Total Series (Univariate analysis)

|  | % RFS | % P | % CCS | % P |
|---|---|---|---|---|
| BAG1− | 26 | 0.05 | 34 | 0.05 |
| BAG1+ | 29 |  | 42 |  |
| Control | 22 | 0.003 | 28 | 0.01 |
| CMF | 31 |  | 43 |  |
| Premenop | 27 | 0.67 | 39 | 0.42 |
| Postmenop | 27 |  | 34 |  |
| T ≦ 2 cm | 29 | 0.20 | 37 | 0.38 |
| T > 2 cm | 25 |  | 36 |  |
| N + 1 − 3 | 31 | 0.0002 | 41 | 0.0007 |
| N + > 3 | 19 |  | 28 |  |
| ER+ | 26 | 0.58 | 38 | 0.02 |
| ER− | 29 |  | 34 |  |
| BCL2+ | 26 | 0.94 | 37 | 0.26 |
| BCL2− | 34 |  | 37 |  |

Legends:
RFS (relapse-free survival)
CCS (cause specific survival)

When the 179 women treated with surgery alone were evaluated separately, again higher levels of BAG1 immunopositivity were associated with longer RFS and CSS (p=0.027 for RFS; p=0.039 for CSS) in univariate analysis (Table 3). For example, 28% of patients whose tumors exhibited high BAG1 immunostaining were relapse-free at 20 years after initial diagnosis and therapy, compared to only 19% of patients whose tumors had low BAG1 expression (Table 3). BAG1 immunostaining data, however, were not significantly correlated with survival when the 209 patients who received adjuvant chemotherapy were examined separately, suggesting that BAG1 looses its prognostic significance in this setting.

TABLE 3

Results at 20 yrs
Control (Surgery only; Univariate analysis)

|  | % RFS | % P | % CCS | % P |
|---|---|---|---|---|
| BAG1− | 19 | 0.027 | 23 | 0.039 |
| BAG1+ | 28 |  | 38 |  |
| Premenop | 20 | 0.23 | 25 | 0.25 |
| Postmenop | 24 |  | 32 |  |
| T ≦ 2 cm | 24 | 0.14 | 28 | 0.46 |
| T > 2 cm | 21 |  | 29 |  |
| N + 1 − 3 | 25 | 0.009 | 30 | 0.04 |
| N + >3 | 17 |  | 27 |  |
| ER+ | 20 | 0.70 | 30 | 0.038 |
| ER− | 27 |  | 27 |  |

TABLE 3-continued

Results at 20 yrs
Control (Surgery only; Univariate analysis)

|  | % RFS | % P | % CCS | % P |
|---|---|---|---|---|
| BCL2+ | 21 | 0.95 | 28 | 0.76 |
| BCL2− | 29 |  | 33 |  |

Multivariate analysis (Table 4), using a Cox-regression analysis, also demonstrated a significant correlation of higher levels of BAG1 immunostaining with longer CSS when all 342 patients were considered together (p=−0.046). BAG1 was also significantly associated with longer CSS (p=0.022) when patients treated with surgery alone (179) were evaluated, but not among the subgroup of patients who received adjuvant therapy. Thus, BAG1 is an independent predictor of RFS and CSS in women with node-positive breast cancer who do not receive adjuvant chemotherapy after surgery, even when other variables are considered, including extent of nodal involvement, menopausal status, and ER status.

TABLE 4

BAG1 CASE SERIES
RESULTS AT 20 YRS

| Total Series |  | HR (95% CI) | P |
|---|---|---|---|
| COX REGRESSION ANALYSIS |  |  |  |
| RFS | Treatment | 0.66(0.51-0.86) | 0.0021 |
|  | Nodal extent | 1.65(1.25-2.17) | 0.0003 |
|  | BAG1 | 1.30(0.98-1.73) | 0.064 |
| CCS | Treatment | 0.67(0.51-0.90) | 0.0068 |
|  | Nodal extent | 1.61(1.20-2.16) | 0.0015 |
|  | BAG1 | 1.37(1.01-1.87) | 0.046 |
|  | ER | 0.67(0.49-0.91) | 0.011 |
| CONTROL (Surgery Only) |  |  |  |
| RFS | Nodal extent | 1.59(1.05-2.39) | 0.028 |
|  | BAG1 | 1.44(0.96-2.17) | 0.079 |
| CCS | BAG1 | 1.68(1.08-2.63) | 0.022 |
|  | ER | 0.55(0.35-0.86) | 0.008 |
| CMF |  |  |  |
| RFS | Nodal extent | 1.77(1.23-2.56) | 0.0023 |
| CCS | Nodal extent | 1.86(1.24-1.78) | 0.0025 |
|  | Menopause | 1.54(1.01-2.29) | 0.055 |

3.0 Immunohistochemical Analysis of BAG1 in Prostate Cancer

Pathological Elevations in BAG1L in Prostate Cancers.

Immunohistochemical methods were used to evaluate the expression of the BAG1N (cytosolic) and BAG1L (nuclear) proteins in primary and metastatic prostate cancer specimens. Previously it was determined that BAG1N is cytosolic while BAG1L is nuclear (BAG1N is referred to as BAG-1 in Takayama et al. 1998, *Cancer Res.* 58:3116-3131) and (Packham et al. 1997, *Biochem. J.* 328:807-813). Using anti-BAG1 monoclonal antibodies (Takayama et al. 1998, supra), immunohistochemical methods and archival paraffin-embedded prostate cancer specimens were used to evaluate the expression of the nuclear (BAG1L) and cytosolic (BAG1N) proteins in over 800 cases of prostate cancer. Comparisons were made with BAG1 immunostaining results in normal prostate and benign prostatic hypertrophy. Tissue microarray technology was exploited for much of this analysis, permitting the analysis large numbers of tumor specimens (Kononen et al. 1998, *Nature Med.* 4:844-847).

Compared to normal prostate, cytosolic BAG1N immunostaining was elevated in 746 of 876 (85%) of prostate cancers. Nuclear BAG1 (BAG1L) immunostaining was inappropriately increased in 171 of 676 (25%) of prostate cancers, compared to normal prostate gland epithelium. Clinical follow-up data or other types of laboratory information were available for some of these patients, demonstrating a variety of correlations of BAG1 expression with more aggressive tumor phenotypes. For example, in a cohort of 62 patients with early-stage (T1,T2) disease and low Gleason grade (gr 2-6), higher percentages of BAG1 immunopositive tumor cells were associated with higher PSA levels prior to radiation therapy (p=0.05), and with a higher incidence of distant metastases after therapy (p=0.05). Higher intensity BAG1 immunostaining was also associated with a higher incidence of metastatic relapse after radiation therapy (p<0.0001). In addition, immunohistochemical analysis of 722 prostate cancer specimens in a microarray format revealed higher percentages of BAG1 immunopositive cells in tumors (n=722) compared to normal prostate (n=54): mean+SE: 41+3% normal versus 78+1% cancer (p<0.0001). An association was also identified between higher percentages of BAG1 immunopositive tumor cells and locally advanced disease (p=0.05) (n=625 patients) and with hormone refractory disease (p<0.001) (n ~263 patients).

Higher percentages of tumor cells with nuclear BAG1-immunostaining (BAG1L) as well as higher intensity nuclear BAG1L (BAG1L intensity) staining were also associated with hormone-refractory disease: p<0.001 and p<0.0001, respectively (n=263). Higher intensity BAG1 nuclear immunostaining was also correlated with hormone-refractory (HR) disease in a cohort of 92 prostate cancer patients with locally-advanced disease who were treated with anti-androgen therapy prior to surgery (50% vs 9% HR; p<0.001).

From these observations, three conclusions can be reached. First, tumor-specific increases in cytosolic BAG1 and nuclear BAG1L levels commonly occur in prostate cancers. Second, immunohistochemical analysis of BAG1N (cytosolic) and BAG1L (nuclear) expression provides prognostic information about prostate cancer patients, including information about progression to hormone-refractory disease. Third, unlike the situation with breast cancer, higher levels of cytosolic BAG1N expression are associated with unfavorable prognosis rather than favorable prognosis.

Although the invention has been described with reference to the disclosed embodiments, it should be understood that various modifications can be made without departing from the spirit of the invention. Accordingly, the invention is limited only by the following claims.

I claim:

1. A method for determining the risk of tumor recurrence or spread in a patient suffering from prostate cancer, said method comprising:
    (a) determining a cytosolic BAG-1 protein level in a cancerous prostate tissue sample from said patient; and
    (b) comparing said cytosolic BAG-1 protein level in said sample to a reference cytosolic BAG-1 protein level, said reference level being a level of cytosolic BAG-1 protein above which correlates with an increased risk of tumor recurrence or spread and below which correlates with a decreased risk of tumor recurrence or spread, thereby determining the risk of tumor recurrence or spread in said patient.

2. The method of claim 1, wherein said tumor spread comprises tumor metastasis.

3. The method of claim 1, wherein said cytosolic BAG-1 protein level is determined with an antibody specific for BAG-1 protein.

4. The method of claim 1, wherein said cytosolic BAG-1 protein comprises BAG-1N and BAG-1M.

5. The method of claim 1, wherein said cytosolic BAG-1 protein level is determined using an immunoassay.

6. The method of claim 5, wherein said immunoassay is an immuno-polymerase chain reaction (immuno-PCR) assay.

7. The method of claim 1, wherein said reference cytosolic BAG-1 protein level is a level of cytosolic BAG-1 protein above which correlates with increased risk of tumor recurrence or spread in a first group of patients compared to a second group of patients, said second group of patients having cytosolic BAG-1 protein levels below said reference level.

8. A method for determining a prognosis of survival in a patient suffering from prostate cancer, said method comprising:
    (a) determining a cytosolic BAG-1 protein level in a cancerous prostate tissue sample from said patient; and
    (b) comparing said cytosolic BAG-1 protein level in said sample to a reference cytosolic BAG-1 protein level, said reference level being a level of cytosolic BAG-1 protein above which correlates with decreased survival and below which correlates with increased survival, thereby determining a prognosis of survival in said patient.

9. The method of claim 8, wherein said survival is overall survival.

10. The method of claim 8, wherein said survival is distant metastasis-free survival.

11. The method of claim 8, wherein said cytosolic BAG-1 protein level is determined with an antibody specific for BAG-1 protein.

12. The method of claim 8, wherein said cytosolic BAG-1 protein comprises BAG-1N and BAG-1M.

13. The method of claim 8, wherein said cytosolic BAG-1 protein level is determined using an immunoassay.

14. The method of claim 13, wherein said immunoassay is an immuno-polymerase chain reaction (immuno-PCR) assay.

15. The method of claim 8, wherein said reference cytosolic BAG-1 protein level is a level of cytosolic BAG-1 protein above which correlates with decreased survival in a first group of patients compared to a second group of patients, said second group of patients having cytosolic BAG-1 protein levels below said reference level.

* * * * *